| United States Patent [19] | [11] Patent Number: 4,760,186 |
|---|---|
| Solodar | [45] Date of Patent: Jul. 26, 1988 |

[54] PREPARATION OF SUBSTITUTED AROMATIC AMINES

[75] Inventor: A. John Solodar, University City, Mo.

[73] Assignee: Monsanto Company, St. Louis, Mo.

[21] Appl. No.: 907,278

[22] Filed: Sep. 15, 1986

[51] Int. Cl.$^4$ .............................................. C07C 85/00
[52] U.S. Cl. .................................. 564/415; 564/434; 564/435
[58] Field of Search ..................... 564/415, 434, 435; 534/587, 578

[56] References Cited

FOREIGN PATENT DOCUMENTS 1440767 6/1976 United Kingdom ................ 564/435

OTHER PUBLICATIONS

Wawzonek et al., *Chemical Abstracts*, vol. 67, No. 22, Abstract 104599b, (1967).
Sidgwick, N. V., *The Organic Chemistry of Nitrogen*, Clarendon Press, Oxford, pp. 149–154, 578–579, (1967).

*Primary Examiner*—Glennon H. Hollrah
*Assistant Examiner*—John A. Sopp
*Attorney, Agent, or Firm*—Linda L. Lewis; James W. Williams, Jr.

[57] ABSTRACT

A process for the preparation of substituted aromatic amines comprising (1) contacting a primary aromatic amine with an oxidizing agent in a homogeneous solution containing water, an oxidizable water-miscible organic solvent and a base, and (2) reducing the solution with a reducing agent to produce the substituted aromatic amine.

13 Claims, No Drawings

PREPARATION OF SUBSTITUTED AROMATIC AMINES

FIELD OF THE INVENTION

The invention relates to a process for the preparation of substituted aromatic amines. More specifically, the invention relates to the preparation of aminodiphenylamines.

DESCRIPTION OF RELATED ART

British Pat. No. 1,440,767 describes the direct synthesis of 4-aminodiphenylamine (4-ADPA) by the head-to-tail coupling of aniline by oxidation with ferricyanide followed by hydrogenation. This process has numerous disadvantages. The oxidation step occurs in a two-phase system containing an oxidation-resistant organic solvent, typically a chlorinated solvent. Environmental concerns require the reduction or elimination of the use of such chlorinated solvents. Additionally, intense mixing is required to keep the two-phase in contact. Finally, the overall selectivities to 4-ADPA are relatively low, in the range of about 9 to 37% based on aniline consumed after the hydrogenation step.

SUMMARY OF THE INVENTION

A process for the preparation of substituted aromatic amines of the formula

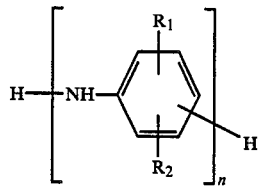

wherein n equals from 2 to 5, $R_1$ and $R_2$ are either the same or different aliphatic radicals or hydrogen, which comprises (1) contacting a primary aromatic amine with an oxidizing agent in a homogeneous solution containing water, an oxidizable water-miscible organic solvent and a base, and (2) reducing the solution with a reducing agent to form the substituted aromatic amine.

The present invention is an improvement over BP 1,440,767, in that it allows the use of oxidizable organic solvents in the oxidation step, thereby eliminating the use of environmentally hazardous chlorinated organic compounds. In addition, the oxidation occurs in a homogeneous solution, which eliminates the need for intense mixing and special reactor design. Finally, the process provides a method of preparing quantities of substituted aromatic amines in much higher selectivities than produced by the methods taught in BP 1,440,767, e.g. in the range of about 25 to 71% based on aniline consumed after the hydrogenation step.

DETAILED DESCRIPTION OF THE INVENTION

The improved process involves two steps: the oxidation of a primary aromatic amine and its reduction to form substituted aromatic amines. The substituted amines are oligomers of the primary aromatic amines where n equals from 2 to 5 and $R_1$ and/or $R_2$ are hydrogen or the same or different aliphatic radicals.

In the first step, a primary aromatic amine is oxidized to form a mixture of oxidation products which includes some products where benzene rings are bound by azo linkages. The oxidation step is carried out by mixing the amine or a solution of the amine in a homogeneous solution containing water, an oxidizable water-miscible organic solvent, an oxidizing agent and a strong base.

Suitable primary aromatic amines are of the structure

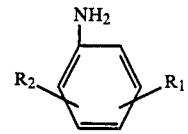

where $R_1$ and $R_2$ are either the same or different aliphatic radicals or hydrogen. Examples of such primary aromatic amines include 2-methyl aniline, 2-ethyl aniline and 2,6-dimethyl aniline. The preferred amine is aniline, a readily available commodity chemical.

The oxidation step is carried out with an oxidizing agent and a base in a homogeneous solution containing water and an oxidizable water-miscible organic solvent. The organic solvent can be any of a number of water-miscible organic solvents such as alcohols, e.g. methanol, ethanol, propanol, isopropanol, butanol, 2-butanol; nitriles such as acetonitrile; ethers such as polyethylene glycols; ketones such as methylethyl ketone and acetone; and other solvents such as tetrahydrofuran. If the desired product is the para-position polymer exclusive of other isomers, e.g. 4-ADPA, then the preferred solvent is methanol, which produces the almost pure para-isomer. If it is desired to maximize selectivity to the para-isomer and produce a mixture of isomers, e.g. a mixture of ortho- and para-isomers, the 1-propanol solvent is preferred.

The ratio of solvent to water in the oxidation step can be varied widely, in the range of about 5:95 to 95:5 volume ratio, with the preferred volume ratios being in the range of 40:60 to 60:40, which improves the selectivity to the para-position isomer, the most preferred being 50:50. The amount of primary aromatic amine reactant present in the solvent-water solution is very dilute to discourage side reactions, such as polymerization of the substituted amine where n is greater than 5. Typically, the weight ratio of amine to homogeneous solvent solution is in the range of about 0.001 to about 1.20, and the preferred range is about 0.01 to about 0.1, to provide a dilute enough solution to discourage excessive polymerization but high enough concentration to produce an appreciable amount of substituted amine.

The oxidizing agent is an alkali metal ferricyanide, such as potassium ferricyanide or sodium ferricyanide. The preferred alkali metal ferricyanide is potassium ferricyanide. The amount of oxidizing agent used can vary widely. The smaller the amount used, the greater the selectivity to the substituted aromatic amines and the lower the conversion. The greater the amount used, the higher the conversion of the primary aromatic amine but low selectivity to substituted aromatic amine. Typically, the mole ratio of oxidizing agent to primary amine is in the range of about 4:1 to about 1:4, with the preferred ratio being about 1:1 to achieve the desired balance of selectivity and conversion.

The base which is used in the oxidation step can be any of a number of bases, such as sodium hydroxide, potassium hydroxide, ammonium hydroxide, tetramethyl hydroxide, ammonium sodium carbonate and lithium hydroxide, or a mixture of such bases. The minimum amount of base required for the oxidation step is equal molar amounts with the oxidizing agent. Typically, there is some excess of base used, to guarantee that a sufficient amount is present in the reaction system. Therefore, the mole ratio of base to oxidizing agent is in the range of about 1:1 to about 6:1, the preferred range being from about 1:1 to about 2:1.

The oxidation step reaction occurs quickly and the reaction time, therefore, can be very short. If the reaction is allowed to continue for a long period of time, a slow reaction of the substituted amine continues, resulting in polymers where n is greater than 5 and a subsequent loss of selectivity. The reaction time is typically in the range of about 1 to about 60 minutes, with the preferred range being about 15 to about 45 minutes.

The oxidation step reaction can be run at relatively low temperatures, with the best results occurring below about 35° C. At higher temperatures the substituted amines react further to form polymers with n greater than 5 and tars, resulting in a loss of selectivity. The preferred reaction temperature range is about 20° C. to 30° C. The most preferred reaction temperature, because of ease of operation, is room temperature, around 23° C.

Although the oxidation step occurs as a homogeneous system, some mixing is required, because ferrocyanide salts will settle out of the solution. Adequate mixing can be achieved with a magnetic stirrer or a paddle stirrer in the bottom of a round bottom flask.

The second step of the process to make substituted aromatic amines is to reduce the oxidation product. This results in two reactions. One produces the substituted amines from an unidentified intermediate. The second reduces the azobenzene compound to the primary aromatic amine, which can be recovered and recycled. The reduction can be carried out by any of many known reductive processes, such as using a hydride such as sodium borohydride or sodium borohydride in conjunction with palladium- or platinum-on-carbon calatyst. The preferred process is catalytic reduction wherein hydrogenation can be effected under pressure in the presence of platinum-or palladium-on-carbon as catalyst. This process is described in detail in "Catalytic Hydro-genation in Organic Synthesis", P. N. Rylander, Academic Press, N.Y. 1979, p 299, which is hereby incorporated by reference.

EXAMPLES

The following examples are for illustration purposes only and in no way limit the scope of this invention.

In the following examples, oxidation is effected as follows:

At room temperature, the base, as a solid, the oxidant and about one-half of the water is added to a round bottomed flask with stirring. After the solids dissolve, about one-half of the solvent, a solution of the aniline and the other one-half of the solvent, and the remaining water are added. The mixture is stirred for the designated reaction time.

Hydrogenation is effected as follows:

The reaction mixture is placed in an autoclave reactor with 80 ml ethanol and 0.2 g of 5% palladium-on-charcoal catalyst. Hydrogen is added to the reactor and the solution is hydrogenated at 50° C. and 100 psig (689 kPa) for about 30 minutes.

The resulting mixture is analyzed for aniline by gas chromatographic separation on a 30 meter fused silica column of DB wax-30W using either 1-octanol or dodecane as an internal standard. The separation is temperature programmed from 70° to 220° C. at 10°/minute.

The reduction product is analyzed by high pressure liquid chromatography (HPLC) to determine azobenzene, 4-ADPA and 2-ADPA. The analysis is performed on a $C_{18}$ reverse phase (ODS) column using acetonitrile-water as the solvent programmed from 35:65 to 75:25 (volume:volume) acetonitrile:water over 15 minutes at 1.0 ml/minute. Fluoranthene or p-nitrochlorobenzene is used as the internal standard. A Hewlett-Packard Diode Array detector set at 282±15 nanometer was employed for peak detection and integration.

Table I

Examples 1 through 16 are shown in Table I. Examples 1 and 2, 5 and 6, and 15 and 16 illustrate the reproducibility of the process. Examples 3 through 10 illustrate the effect of varying the type of water-miscible organic solvent on conversion and selectivity to 4-ADPA. The methanol solution (Example 3) produces about 100% 4-ADPA (e.g. the para-isomer). The 1-propanol solution (Example 5) produces mixtures containing the highest selectivity to 4-ADPA of the solvent solutions tested. Examples 3, 11, 12 and Control show the effect of varying or eliminating the strong base. Examples 2 and 3, and 5 and 13 show that little difference is seen in increasing the reaction time from 5 to 15 minutes, but some loss of selectivity is observed in an increase of from 15 to 45 minutes.

TABLE I

| | | | | | | | |
|---|---|---|---|---|---|---|---|
| | | | | Varying Solvent | | | |
| Example | Run Time (min) | (1) Solvent | (2) Base | (3) Selectivity (%) | (3) Conversion (%) | Ratio 4-ADPA to 2-ADPA | (3) Material Balance (%) |
| 1 | 5 | | | 44 | 31 | 100/0 | 83 |
| 2 | 5 | | | 45 | 28 | 100/0 | 85 |
| 3 | 15 | | | 48 | 28 | 100/0 | 86 |
| 4 | 15 | (1a) | | 59 | 29 | 89/11 | 91 |
| 5 | 15 | (1b) | | 71 | 26 | 69/31 | 103 |
| 6 | 15 | (1b) | | 65 | 31 | 69/31 | 99 |
| 7 | 15 | (1c) | (2a) | 70 | 27 | 68/32 | 101 |
| 8 | 15 | (1d) | | 62 | 26 | 60/40 | 102 |
| 9 | 15 | (1e) | | 65 | 22 | 63/37 | 102 |
| 10 | 15 | (1f) | | 64 | 20 | 70/30 | 98 |
| 11 | 15 | | (2b) | 40 | 19 | 100/0 | 89 |
| 12 | 15 | | (2c) | 45 | 24 | 100/0 | 87 |
| Control | 15 | | (2d) | 0 | 0 | 100/0 | 101 |

TABLE I-continued

Varying Solvent

| Example | Run Time (min) | (1) Solvent | (2) Base | (3) Selectivity (%) | (3) Conversion (%) | Ratio 4-ADPA to 2-ADPA | (3) Material Balance (%) |
|---|---|---|---|---|---|---|---|
| 13 | 45 | (1b) | | 60 | 32 | 100/0 | 92 |
| 14 | 45 | | (2c) | 59 | 18 | 100/0 | 93 |
| 15 | 45 | (1g) | | 64 | 19 | 100/0 | 93 |
| 16 | 45 | (1g) | | 53 | 16 | 100/0 | 93 |

Oxidant is 6 mmoles of $K_3Fe(CN)_6$, except for example 7 which used 12 mmoles $K_3Fe(CN)_6$, and 6 mmoles of aniline, unless otherwise indicated.
(1) Solvent is 20 ml of methanol and 20 ml of $H_2O$, unless otherwise indicated.
(1a) Solvent is 20 ml of ethanol.
(1b) Solvent is 20 ml of 1-propanol
(1c) Solvent is 20 ml of 2-propanol and 12 ml of aniline used.
(1d) Solvent is 20 ml of 1-butanol
(1e) Solvent is 20 ml of 2 butanol
(1f) Solvent is 20 ml of acetonitrile
(1g) Solvent is 40 ml of methanol and 40 ml of $H_2O$
(2) Base is 7.2 mmoles of NaOH, unless otherwise indicated.
(2a) Base is 14.4 mmoles of NaOH
(2b) Base is 7.2 mmoles of $Na_2CO_3$
(2c) Base is 7.2 mmoles of $(CH_3)_4NOH$
(2d) NaCl is substituted for base (7.2 mmoles)
(3) Calculations are based on aniline rings recovered.

Table II

Examples 17 to 27, shown in Table II, illustrate a wide variety of bases that are effective for the oxidation step.

TABLE II

Varying Base

| Example | Base Type | Selectivity (%) | Conversion (%) | Ratio 4-ADPA to 2-ADPA |
|---|---|---|---|---|
| 17 | LiOH | 49 | 30 | 100/0 |
| 18 | NaOH | 65 | 25 | 87/13 |
| 19 | NaOH | 38 | 38 | 96/4 |
| 20 | KOH | 52 | 32 | 100/0 |
| 21 | Me4NOH | 59 | 18 | 100/0 |
| 22 | Me4NOH | 37 | 14 | 100/0 |
| 23 | LiOH | 51 | 28 | 100/0 |
| 24 | LiOH | 34 | 16 | 100/0 |
| 25 | NaOH | 47 | 36 | 100/0 |
| 26 | NaOH | 52 | 31 | 100/0 |
| 27 | KOH | 45 | 36 | 100/0 |

Run time is 45 minutes. All runs are made with 40 ml each water and methanol, 12 mmoles of $K_3Fe(CN)_6$, 12 mmoles aniline, 14.4 mmoles base.

Table III

Examples 28 through 50, shown in Table III, illustrate the effect of varying the water to solvent volume ratio, the concentration of primary aromatic amine in the reaction mixture and the concentration of base and oxidant in the reaction mixture on selectivity and conversion to 4-ADPA.

TABLE III

Varying Solvent and Reactant Concentrations

| Example | Methanol:H2O (ratio) | Aniline (mmoles) | Base NaOH (mmoles) | Oxidant $K_3Fe(CN)_6$ (mmoles) | Selectivity (%) | Conversion (%) | Ratio 4-ADPA to 2-ADPA |
|---|---|---|---|---|---|---|---|
| 28 | 1.6:1 | 120 | 104.7 | 75.2 | 25 (4) | 41 | 100/0 |
| 29 | 1.6:1 | 60 | 106.8 | 75.0 | 28 (4) | 63 | 97/3 |
| 30 | 1:1 | 12 | 20.2 | 3.1 | 30 | 14 | 100/0 |
| 31 | 0.75:1 | 12 | 48.8 | 12.1 | 30 | 49 | 88/12 |
| 32 | 1:1 | 60 | 106.7 | 45.5 | 31 (5) | 36 | 93/7 |
| 33 | 1:1 | 60 | 105.0 | 45.5 | 36 (6) | 33 | 92/8 |
| 34 | 1:1 | 60 | 106.5 | 45.6 | 36 (6) | 36 | 91/9 |
| 35 | 1:1 | 12 | 21.3 | 15.8 | 42 | 46 | 100/0 |
| 36 | 1:1 | 12 | 30.2 | 15.8 | 43 | 48 | 100/0 |
| 37 | 1:1 | 60 | 107.4 | 45.5 | 43 (7) | 32 | 92/8 |
| 38 | 1:1 | 12 | 16.4 | 12.0 | 45 | 31 | 100/0 |
| 39 | 1.2:1 | 12 | 49.2 | 11.8 | 46 | 33 | 88/12 |
| 40 | 1:1 | 12 | 25.1 | 12.1 | 47 | 36 | 100/0 |
| 41 | 1:1 | 12 | 20.9 | 15.7 | 48 | 42 | 100/0 |
| 42 | 1:1 | 12 | 15.7 | 6.0 | 50 | 14 | 100/0 |
| 43 | 1:1 | 12 | 28.1 | 9.1 | 51 | 26 | 94/6 |
| 44 | 1:1 | 12 | 27.7 | 12.0 (3) | 52 | 31 | 100/0 |
| 45 | 1:1 | 12 | 21.0 | 9.1 | 57 | 21 | 100/0 |
| 46 | 1:1 | 12 | 48.7 | 11.9 | 65 | 25 | 87/13 |
| 47 | 1:1 | 12 | 48.4 (1) | 12.0 | 49 | 30 | 100/0 |
| 48 | 1:1 | 12 | 28.1 (1) | 12.0 | 51 | 28 | 100/0 |
| 49 | 1:1 | 12 | 28.6 (2) | 12.0 | 45 | 36 | 100/0 |
| 50 | 1:1 | 12 | 49.1 (2) | 11.9 | 52 | 32 | 100/0 |
| 51 | 1:1 | 12 | 20.2 | 3.1 | 30 | 14 | 100/0 |
| 52 | 1:1 | 12 | 15.7 | 6.0 | 50 | 14 | 100/0 |
| 53 | 1:1 | 12 | 28.1 | 9.1 | 51 | 26 | 94/6 |
| 54 | 1:1 | 12 | 21.0 | 9.1 | 57 | 21 | 100/0 |

TABLE III-continued

Varying Solvent and Reactant Concentrations

| Example | Methanol: H₂O (ratio) | Aniline (mmoles) | Base NaOH (mmoles) | Oxidant K₃Fe(CN)₆ (mmoles) | Selectivity (%) | Conversion (%) | Ratio 4-ADPA to 2-ADPA |
|---|---|---|---|---|---|---|---|
| 55 | 1.2:1 | 12 | 49.2 | 11.8 | 46 | 33 | 88/12 |
| 56 | 1:1 | 12 | 48.7 | 11.9 | 65 | 25 | 87/13 |
| 57 | 1:1 | 12 | 16.4 | 12.0 | 45 | 31 | 100/0 |
| 58 | 1:1 | 12 | 27.7 | 12.0 (3) | 52 | 31 | 100/0 |
| 59 | 0.75:1 | 12 | 48.8 | 12.1 | 30 | 49 | 88/12 |
| 60 | 1:1 | 12 | 25.1 | 12.1 | 47 | 36 | 100/0 |
| 61 | 1:1 | 12 | 20.9 | 15.7 | 48 | 42 | 100/0 |
| 62 | 1:1 | 12 | 21.3 | 15.8 | 42 | 46 | 100/0 |
| 63 | 1:1 | 12 | 30.2 | 15.8 | 43 | 48 | 100/0 |
| 64 | 1:1 | 60 | 106.7 | 45.5 | 31 | 36 | 93/7 |
| 65 | 1:1 | 60 | 105.0 | 45.5 | 36 | 33 | 92/8 |
| 66 | 1:1 | 60 | 107.4 | 45.5 | 43 | 32 | 92/8 |
| 67 | 1:1 | 60 | 106.5 | 45.6 | 36 | 36 | 91/9 |
| 68 | 1.6:1 | 60 | 106.8 | 75.0 | 28 | 63 | 97/3 |
| 69 | 1.6:1 | 120 | 104.7 | 75.2 | 25 | 41 | 100/0 |
| 70 | 1:1 | 12 | 48.4 (1) | 12.0 | 49 | 30 | 100/0 |
| 71 | 1:1 | 12 | 28.1 (1) | 12.0 | 51 | 28 | 100/0 |
| 72 | 1:1 | 12 | 49.1 (2) | 11.9 | 52 | 32 | 100/0 |
| 73 | 1:1 | 12 | 28.6 (2) | 12.0 | 45 | 36 | 100/0 |

All runs are at room temperature except as indicated. The run time is 45 minutes.
The volume of water used was 40 ml.
(1) LiOH as base
(2) KOH as base
(3) Na₃Fe(CN)₆ as oxidant
(4) Start-up at 10° C., maximum 21° C., mostly 20° C.
(5) Maximum 33° C.
(6) Maximum 16° C., mostly 15° C.
(7) Maximum 22° C., mostly 21° C.

I claim:

1. A process for the preparation of substituted aromatic amines of the formula

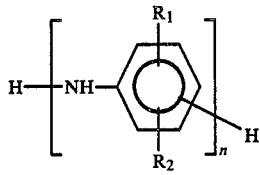

wherein n equals from 2 to 5, $R_1$ and $R_2$ are either the same or different aliphatic radicals or hydrogen, which comprises (1) contacting a primary aromatic amine with an alkali metal ferricyanide oxidizing agent in a homogeneous solution containing water, and oxidizable water-miscible organic solvent and a base, and (2) reducing the solution with a reducing agent to produce the substituted aromatic amine.

2. The process of claim 1 wherein the primary aromatic amine is of the structure

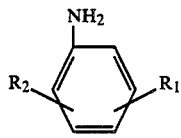

where $R_1$ and $R_2$ are either the same or different aliphatic radicals or hydrogen.

3. The process of claim 2 wherein the primary aromatic amine is aniline.

4. The process of claim 1 wherein the oxidizing agent is an alkali metal ferricyanide.

5. The process of claim 3 wherein n equals 2 and the substituted aromatic amine comprises 4-aminodiphenylamine or 2-aminodiphenylamine or a mixture thereof.

6. The process of claim 3 wherein the oxidizable water-miscible organic solvent is selected from the group consisting of methanol, ethanol, 1-propanol, 1-butanol, 2-propanol, 2-butanol and acetonitrile.

7. The process of claim 5 wherein the volume ratio of solvent to water is in the range of 5:95 to 95:5.

8. The process of claim 5 wherein the weight ratio of aniline to homogeneous solution containing water and solvent is in the range of about 0.001 to about 1.20.

9. The process of claim 5 wherein the mole ratio of oxidizing agent to primary amine is in the range of about 4:1 to about 1:4.

10. The process of claim 5 wherein the mole ratio of base to oxidizing agent is in the range of about 1:1 to about 4:1.

11. The process of claim 5 wherein the oxidation step is run at a temperature of less than 35° C.

12. The process of claim 5 wherein the reducing agent is a palladium-on-carbon catalyst.

13. A process for the preparation of 4-aminodiphenylamine or 2-aminodiphenylamine or a mixture thereof comprising (1) contacting aniline with an alkali metal ferricyanide oxidizing agent in a homogeneous solution containing water and an alcohol selected from the group consisting of methanol, ethanol, 1-propanol and 2-propanol and a base at a temperature below 35° C., and (2) reducing the solution using catalytic reduction to produce the 4-aminodiphenylamine or 2-aminodiphenylamine or the mixture thereof.

* * * * *